(12) United States Patent
Schrader et al.

(10) Patent No.: US 11,744,718 B2
(45) Date of Patent: Sep. 5, 2023

(54) METHOD OF TRIALING AN ORTHOPAEDIC PROSTHETIC ASSEMBLY

(71) Applicant: DePuy Ireland Unlimited Company, Ringaskiddy (IE)

(72) Inventors: Adam D. Schrader, Columbia City, IN (US); William Muhammad, Warsaw, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 496 days.

(21) Appl. No.: 16/934,533

(22) Filed: Jul. 21, 2020

(65) Prior Publication Data
US 2020/0345519 A1  Nov. 5, 2020

Related U.S. Application Data

(62) Division of application No. 15/937,106, filed on Mar. 27, 2018, now Pat. No. 10,716,686.

(51) Int. Cl.
| | | |
|---|---|---|
| *A61F 2/46* | (2006.01) | |
| *A61F 2/38* | (2006.01) | |
| *A61F 2/30* | (2006.01) | |

(52) U.S. Cl.
CPC .......... *A61F 2/4684* (2013.01); *A61F 2/3859* (2013.01); *A61F 2/384* (2013.01); *A61F 2/389* (2013.01); *A61F 2002/3052* (2013.01); *A61F 2002/30331* (2013.01); *A61F 2002/30367* (2013.01); *A61F 2002/30505* (2013.01); *A61F 2002/30576* (2013.01)

(58) Field of Classification Search
CPC ........ A61F 2/4684; A61F 2/38; A61F 2/3836; A61F 2/384; A61F 2/3845; A61F 2/385; A61F 2/3854; A61F 2/3859; A61F 2/3868; A61F 2/3886; A61F 2/389
See application file for complete search history.

(56) References Cited

U.S. PATENT DOCUMENTS

| | | | |
|---|---|---|---|
| 4,215,439 | A | 8/1980 | Gold et al. |
| 5,910,171 | A | 6/1999 | Kummer et al. |
| 10,716,686 | B2 | 7/2020 | Schrader et al. |
| 2017/0049582 | A1 | 2/2017 | Braun et al. |

FOREIGN PATENT DOCUMENTS

| | | |
|---|---|---|
| EP | 0716839 A1 | 6/1996 |
| EP | 0724868 A1 | 8/1996 |
| EP | 2939615 A1 | 11/2015 |
| FR | 2601873 A1 | 1/1988 |
| FR | 2776919 A1 | 10/1999 |
| RU | 2080840 C1 | 6/1997 |
| UA | 85954 C2 | 3/2009 |

OTHER PUBLICATIONS

Extended European Search Report for Application No. 19162532.6, dated Jul. 29, 2019, 9 pages.
Russian Search Report for Application No. 2019107936, dated Nov. 15, 2021, 2 pages.

*Primary Examiner* — Marcia L Watkins
(74) *Attorney, Agent, or Firm* — BARNES & THORNBURG LLP (57) ABSTRACT

An orthopaedic surgical instrument system includes a tibial base trial and a tibial insert trial. An insert adaptor is sized to be positioned in an aperture defined in the tibial insert trial. The insert adaptor includes a base sized to be positioned over a post of the tibial base trial and a locking tab positioned in the base and configured to engage the post of the tibial base trial.

17 Claims, 8 Drawing Sheets

METHOD OF TRIALING AN ORTHOPAEDIC PROSTHETIC ASSEMBLY

This application is a divisional application and claims priority to U.S. patent application Ser. No. 15/937,106, now U.S. Pat. No. 10,716,686, which was filed on Mar. 27, 2018, the entirety of which is expressly incorporated herein by reference.

TECHNICAL FIELD

The present disclosure relates generally to orthopaedic surgical instruments, and particularly to a tibial trial component for use in trialing an orthopaedic prosthetic.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. In a revision knee surgery, the previously-implanted knee prosthesis, sometimes referred to as a "primary knee prosthesis," is surgically removed and a replacement or revision knee prosthesis is implanted. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur During joint arthroplasty, trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a stem trial that may be used to size and select a prosthetic stem component.

SUMMARY

According to an aspect of the disclosure, an orthopaedic surgical instrument system includes a tibial base trial including a plate configured to be positioned on a proximal end of a patient's tibia and a post extending outwardly from a superior surface of the plate. A tibial insert trial includes an inferior surface configured to abut the superior surface of the plate. The tibial insert trial also includes a pair of curved surfaces positioned opposite the inferior surface. The tibial insert trial also includes a spine positioned between the pair of curved surfaces. The tibial insert trial also includes an aperture defined in the inferior surface. An insert adaptor is sized to be positioned in the aperture defined in the tibial insert trial. The insert adaptor includes a base sized to be positioned over the post of the tibial base trial and a locking tab positioned in the base. The post of the tibial base trial includes a superior flange configured to engage the locking tab of the insert adaptor to prevent movement of the insert adaptor in an inferior-superior direction relative to the tibial base trial.

In some embodiments, a channel may be defined between the superior flange and the superior surface of the plate. The locking tab may be sized to be positioned in the channel. The post may include a stem extending outwardly from the plate to the superior flange. The locking tab may include a pair of arms configured to engage the stem of the post. Each arm of the pair of arms may be a spring clip.

In some embodiments, the tibial insert trial may include a first posterior slot that opens into the aperture. The insert adaptor may have a second posterior slot positioned superior of the locking tab. The insert adaptor may be positioned in the aperture defined in the tibial insert trial. The first posterior slot and the second posterior slot may be aligned to define a posterior passageway sized to receive the superior flange of the post to permit the insert adaptor and the tibial insert trial to move in an anterior-posterior direction relative to the tibial base trial. The post may include a stem extending outwardly from the plate to the superior flange. The locking tab may include a spring clip configured to engage the stem of the post. The insert adaptor may include a curved wall that defines an inferior section of aperture. The spring clip may be positioned in the inferior section of the aperture and may be spaced apart from the curved wall. The locking tab may include a trunk extending inwardly from the curved wall to the spring clip.

In some embodiments, the insert adaptor may include a plug extending outwardly from the base. The plug may be configured to prevent relative rotation between the insert adaptor and the tibial insert trial. The plug may include a planar outer surface that is configured to engage a planar inner surface of the tibial insert trial to prevent relative rotation between the insert adaptor and the tibial insert trial.

In some embodiments, a femoral component may include a pair of curved surfaces configured to abut the curved surfaces of the tibial insert trial. The femoral component may also include a pair of transverse bores extending in a medial medial-lateral direction through the femoral component. An elongated pin may be sized to be positioned in the transverse bores. The spine of the tibial insert trial may include a bore extending in the medial-lateral direction that is sized to receive the elongated pin to couple the femoral component to the tibial insert trial. The femoral prosthetic component may be configured to articulate relative to the tibial insert trial over a range of motion including extension and flexion. The tibial insert trial and the insert adaptor may be configured to rotate about an axis extending through the post of the tibial base trial.

In some embodiments, the tibial insert trial may have a pin extending from a superior end wall of the aperture defined in the tibial insert trial. The insert adaptor may have a plug extending outwardly from the base. An aperture may be defined through the plug. The pin of the tibial insert trial may be received in the aperture defined through the plug when the insert adaptor is positioned in the aperture defined in the tibial insert trial. A retention mechanism may extend through the plug into the aperture defined through the plug. The retention mechanism may engage an outer surface of the pin when the insert adaptor is positioned in the aperture defined in the tibial insert trial.

According to another aspect of the disclosure, an orthopaedic surgical instrument system includes a tibial base trial including a plate configured to be positioned on a proximal end of a patient's tibia and a post extending outwardly from a superior surface of the plate to a superior flange. A tibial trial component is configured to be positioned over the post of the tibial base trial. The tibial trial component includes an inferior surface configured to abut the superior surface of the plate and a pair of curved surfaces positioned opposite the inferior surface. The tibial trial component also includes a spine positioned between the pair of curved surfaces. The tibial trial component includes a posterior passageway sized to receive the superior flange of the post to permit the tibial trial component to move in an anterior-posterior direction relative to the tibial base trial.

In some embodiments, a locking mechanism may include a locking tab coupled to the tibial insert trial and the superior flange of the post. The tibial trial component may include a first modular component and a second modular component. The superior flange of the post may be configured to engage the locking tab to prevent movement of the first modular component in an inferior-superior direction relative to the tibial base trial. The locking tab may include a spring clip.

In some embodiments, the first modular component may be an insert adaptor and the second modular component may be one tibial insert trial of a plurality of tibial insert trials. Each tibial insert trial may be configured to be selectively coupled to the insert adaptor.

In some embodiments, a femoral component may include a pair of curved surfaces configured to abut the curved surfaces of the tibial insert trial, and a pair of transverse bores extending in a medial medial-lateral direction through the femoral component. An elongated pin may be sized to be positioned in the transverse bores. The spine of the tibial insert trial may include a bore extending in the medial-lateral direction that is sized to receive the elongated pin to couple the femoral component to the tibial insert trial.

According to yet another aspect of the disclosure, a method of trialing an orthopaedic prosthetic assembly includes aligning a tibial trial component with a tibial base trial positioned on a proximal end of a patient's tibia. The method also includes advancing the tibial trial component posteriorly to move a post of the tibial base trial component into a posterior passageway defined in the tibial trial component. The method also includes coupling the tibial trial component to the tibial base trial component such that the tibial trial component is permitted to rotate relative to the tibial base trial. The method also includes aligning a pair of transverse bores defined in a femoral component with a bore defined in a spine of the tibial trial component. The method also includes advancing an elongated pin through the transverse bores and the spine of the tibial trial component to couple the femoral component to the tibial trial component. The method also includes moving the patient's joint through a range of motion including extension and flexion to evaluate a configuration of the orthopaedic prosthetic assembly corresponding to the tibial base trial and the tibial trial component.

In some embodiments, the method may require moving a tibial insert trial of the tibial trial component in a superior direction to detach the tibial insert trial from an insert adaptor of the tibial trial component and the tibial trial component. The method may also require selecting a second tibial insert trial having a different size from the tibial insert trial. The method may also require moving the second tibial insert trial in an inferior direction to attach the second tibial insert trial to the insert adaptor of the tibial trial component and the tibial trial component.

In some embodiments, the method may require aligning an insert adaptor of the tibial trial component with a tibial insert trial of the tibial trial component. The method may also require advancing the insert adaptor into an aperture defined in the tibial insert trial to form the tibial trial component.

BRIEF DESCRIPTION

The detailed description particularly refers to the following figures, in which.

DETAILED DESCRIPTION

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
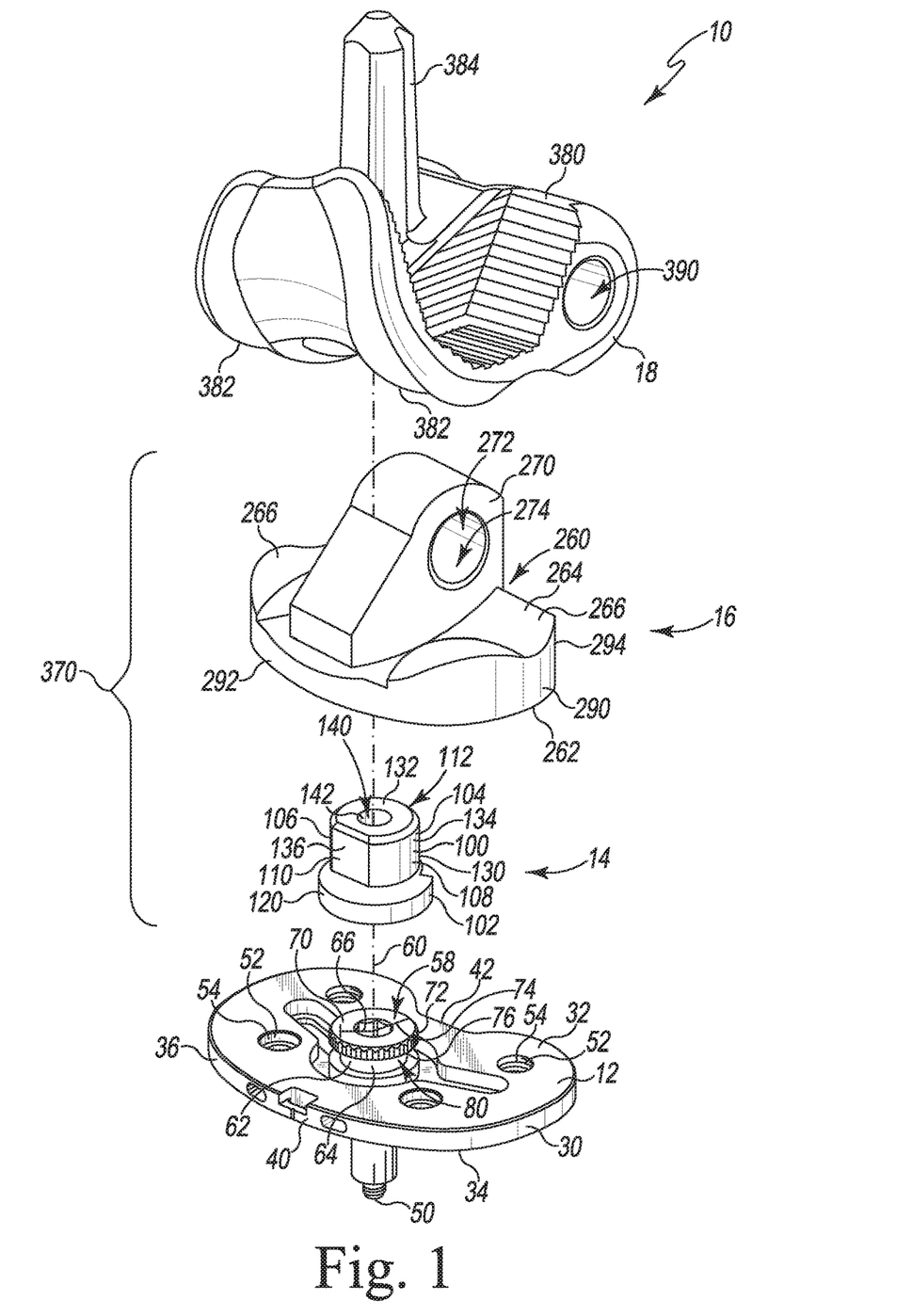
FIG. 1 is an exploded view of an orthopaedic surgical instrument system in accordance with one embodiment.

Referring now to FIG. 1 an orthopaedic surgical instrument system 10 includes a tibial base trial component 12 and a tibial trial component 370 configured to be selectively coupled to the tibial base trial 12. The tibial base trial component 12 and the tibial trial component 370 may be utilized with a femoral component 18 to size and select a tibial prosthesis for implantation into a patient's surgically-prepared tibia. In the illustrative embodiment, the femoral component 18 may be a femoral trial component or a primary femoral component from a previous joint arthroplasty. It should be appreciated that the system 10 may include a number of trial components 12, 370 and femoral trial components of different sizes to accommodate a range of patient anatomies.

As described in greater detail below, the tibial trial component 370 includes an insert adaptor 14 that is configured to removably secure to the tibial base trial 12, and a tibial insert trial 16 that may be positioned on the insert adaptor 14. During a surgical procedure, the surgeon may evaluate the range of motion of the patient's leg with the trial component 12, the trial component 370, and the femoral component 18 positioned in the knee joint, assessing, among other things, the stability of the knee and the displacement of the joint. The tibial insert trial 16 is configured to be detached from the insert adaptor 14 during the surgical procedure and replaced with a tibial insert trial of different size to permit the surgeon to evaluate a range of possible implant sizes and select the one that provides the best performance.

The tibial base trial component 12 is configured to be positioned on a surgically-prepared proximal end of a patient's tibia. In the illustrative embodiment, the base trial 12 includes a plate 30 shaped to be positioned on a proximal end of a patient's tibia. The plate 30 has a superior surface 32, an inferior surface 34, and an outer side wall 36 extending between the surfaces 32, 34. The outer side wall 36 has an anterior section 40 and a posterior section 42 shaped to match a proximal end of a resected tibia. In the illustrative embodiment, the anterior section 40 of the side wall 36 is convexly curved, and the posterior section 42 is concavely curved. It should be appreciated that the tibial base trial 12 may be formed in a number of different sizes to accommodate tibias of various sizes.

The tibial base trial 12 includes a pin 50, which extends downwardly from the inferior surface 34 of the plate 30. The pin 50 is sized to be received in a notch of a surgical instrument inserted into the proximal end of the patient's tibia. Such instruments may include, for example, an elongated broach or stem trial component sized to be positioned in a patient's intramedullary canal. The plate 30 also includes a number of fastener guides 52. Each fastener guide 52 includes a bore 54 configured to receive a fastener such as a fixation pin, which may be utilized to secure the tibial base trial 12 to the proximal end of the patient's tibia.

The tibial base trial 12 includes a post 58 that extends outwardly from the superior surface 32 of the plate 30 along a longitudinal axis 60. The post 58 is configured to secure to the insert adaptor 14. The post 58 includes a stem 62 extending from the superior surface 32 of the plate 30. The stem 62 includes an outer surface 64 having a radius 66 from the longitudinal axis 60 of the post 58. A superior flange 70 extends from a proximal end of the post 58. The superior flange 70 includes an outer surface 72 having a radius 74 from the longitudinal axis 60, wherein the radius 74 is greater than the radius 66. An inferior surface 76 of the superior flange 70 faces the superior surface 32 of the plate 30. A channel 80 is defined between the superior flange 70 and the plate 30. The channel 80 is defined between the inferior surface 76 of the superior flange 70 and the superior surface 32 of the plate 30. As described below, a locking mechanism of the insert adaptor 14 of the tibial trial component 370 is configured to engage the stem 62 of the post 58 within the channel 80.

Figure 2:
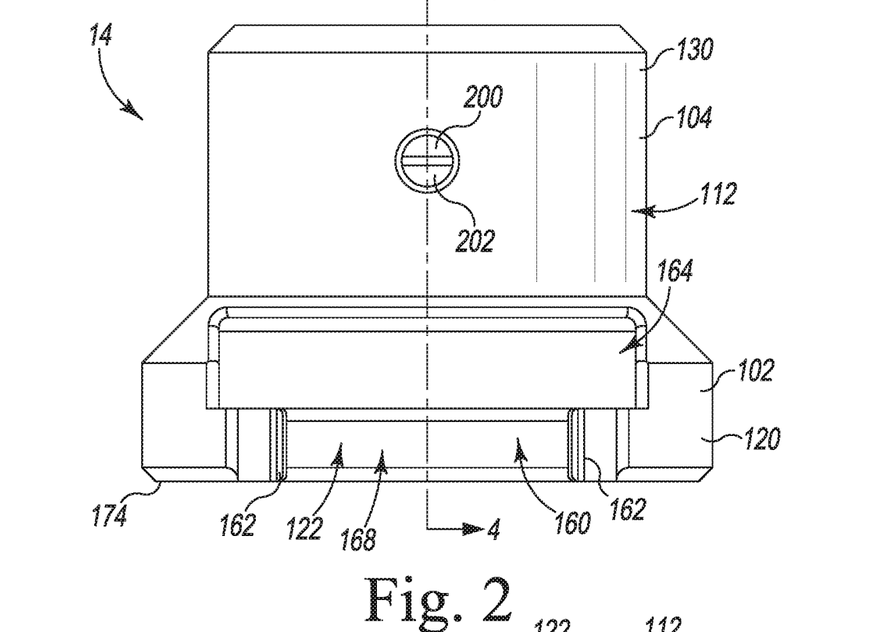
FIG. 2 is a rear elevation view of the insert adaptor shown in FIG. 1.

As shown in FIG. 1, the insert adaptor 14 of the tibial trial component 370 includes a body 100 having a base 102 and a plug 104 extending proximally from the base 102. The base 102 is sized to be positioned over the post 58 of the tibial base trial 12. The base 102 includes an outer surface 120 that curves from a medial side 106, through an anterior side 110, and to a lateral side 108 of the insert adaptor 14. As shown in FIG. 2, an opening 122 is formed in the outer surface 120 of the base 102 on a posterior side 112 of the insert adaptor 14.

Figure 3:
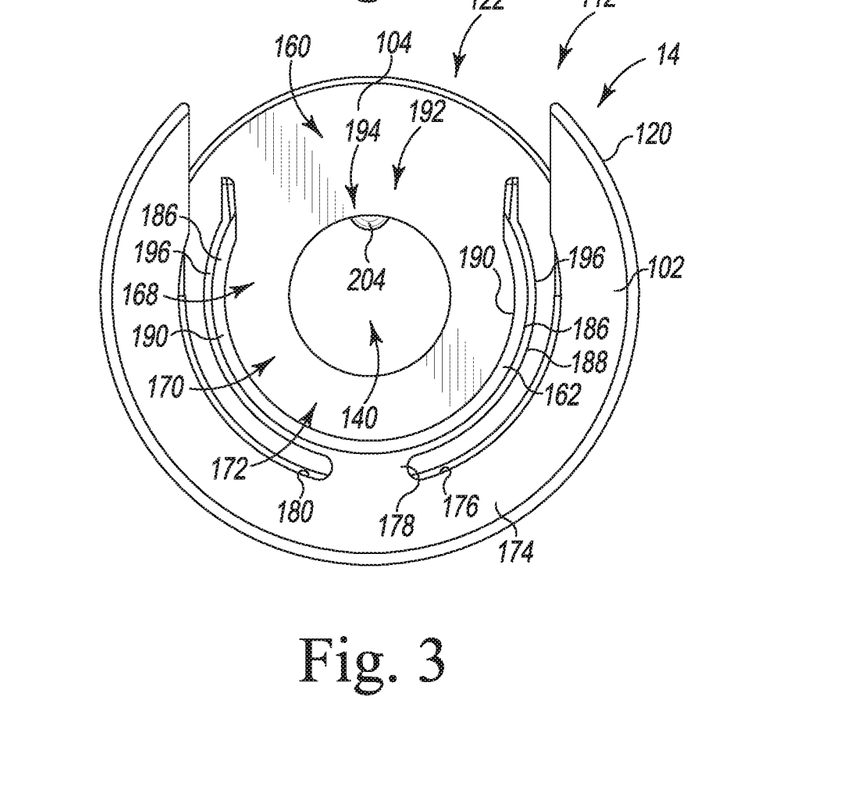
FIG. 3 is a bottom plan view of the insert adaptor shown in FIG. 1.

A cavity 170 extends from an opening 172 in an inferior surface 174 of the insert adaptor 14. A curved inner wall 176 extends from the opening 172 to define the cavity 170. The aperture 140 extends through the plug 104 into the cavity 170. A locking tab 162 is positioned in an inferior section 168 of the cavity 170 and includes a trunk 178 extending from an anterior surface 180 of the curved inner wall 176. The trunk 178 extends posteriorly into the cavity 170. The locking tab 162 also includes a pair of arms 186 extending posteriorly from the trunk 178. The pair of arms 186 includes a medial arm 188 and a lateral arm 190. Each arm 186 includes a curved inner surface 190 that corresponds to the outer surface 64 of the stem 62. An opening 192 is defined between the arms 186. A gap 194 is formed between an outer surface 196 of each arm 186 and the curved inner wall 176. Each arm 186 is configured as a spring clip that can deflect into the respective gap 194 to position the locking tab 162 on the post 58 of the tibial base trial 12. When the insert adaptor 14 is secured to the tibial base trial 12, the arms 186 of the locking tab 162 are configured to position within the channel 80 defined between the superior flange 70 and the plate 30, as described below. The cavity includes a posterior slot 160 extending from the opening 122 formed in the outer surface 120 of the base 102. The locking tab 162 is positioned within the posterior slot 160. Another posterior slot 164 extends from the opening 122 superior to the locking tab 162. As illustrated in FIG. 3, the slots 160 and 164 at least partially define the cavity 170 in the base 102.

Returning to FIG. 2, the plug 104 of the insert adaptor 14 includes an outer wall 130 and a proximal surface 132. The outer wall 130 extends from the base 102 to the proximal surface 132. The outer wall 130 includes a curved surface 134 extending from the medial side 106, through the posterior side 112, and to the lateral side 108. The outer wall 130 also includes a planar anterior surface 136. An aperture 140 extends through the insert adaptor 14 from an opening 142 formed in the proximal surface 132 of the plug 104.

Figure 4:
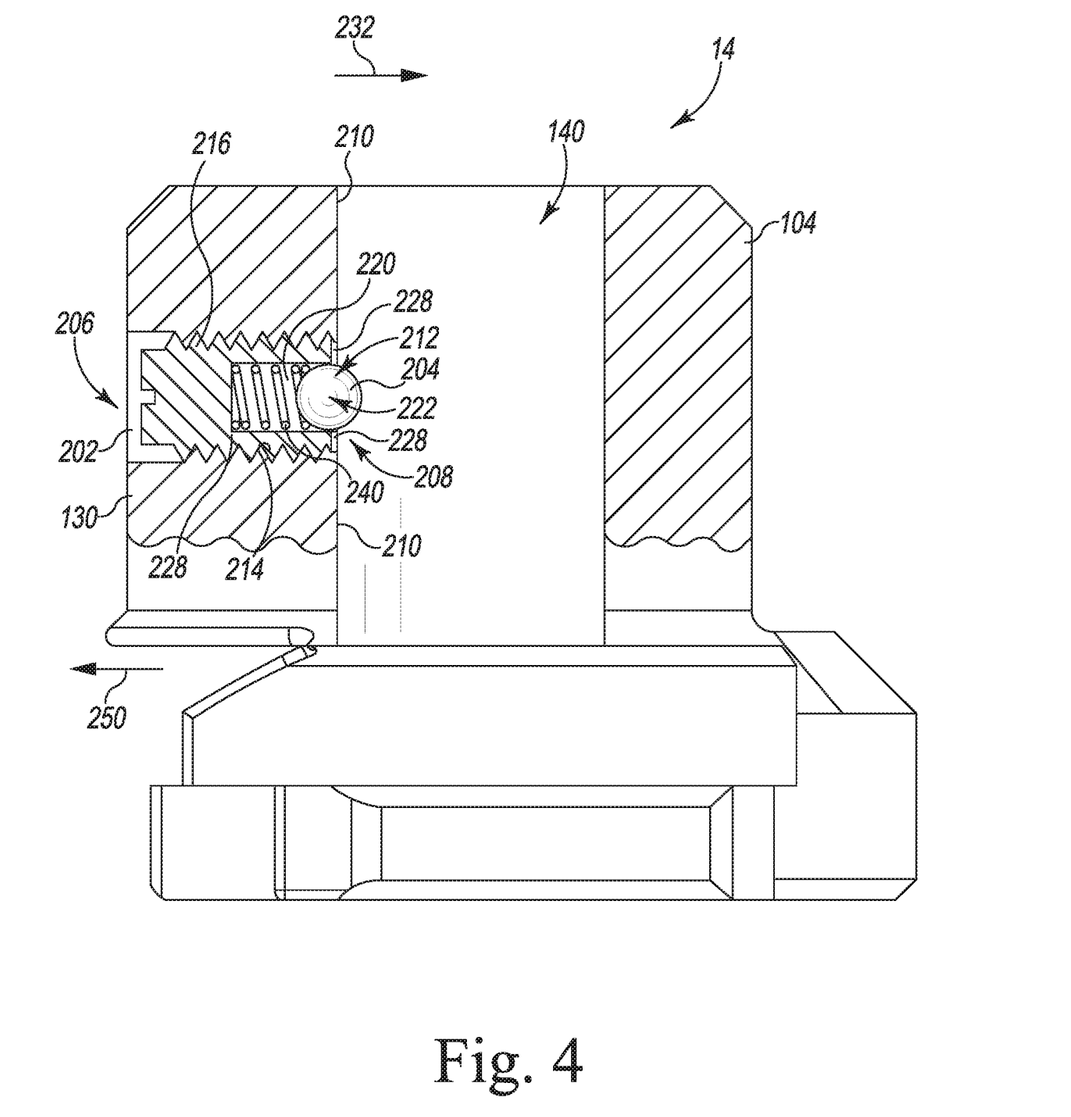
FIG. 4 is a cross-sectional view taken along the line 4-4 in FIG. 2.

A retention mechanism 200 extends through the outer wall 130 of the plug 104. The retention mechanism 200 extends anteriorly from the posterior side 112 of the insert adaptor 14. The retention mechanism 200 includes a screw 202 that secures the retention mechanism 200 within the plug 104, as described in more detail below. As shown in FIG. 4, the retention mechanism 200 includes a ball 204 that extends anteriorly into the aperture 140 of the plug 104. The aperture 140 is defined by an inner surface 210. The plug 104 includes a bore 212 extending between an opening 206 in the outer wall 130 of the plug 104 and an opening 208 in the inner surface 210 of the aperture 140. The bore 212 extends in an anterior-posterior direction.

The bore 212 includes a threaded side wall 214 configured to mate with a threaded body 216 of the screw 202 to secure the retention mechanism within the bore 212. A bore 220 extends from an opening 222 in the threaded body 216 of the screw 202. A spring 240 is retained within the bore 220 and configured to bias the ball 204 in the anterior direction 232. The spring 240 biases the ball 204 in the anterior direction 232 so that the ball 204 engages flanges 228 formed around the opening 222. When a force in the direction of arrow 250 is applied to the ball 204, the ball 204 moves in the posterior direction 250 into the bore 220.

As described above, the tibial trial component 370 includes a tibial insert trial 16 that is configured to be selectively and removably coupled to the insert adaptor 14. Returning to FIG. 1, the tibial insert trial 16 includes a body 260 having an inferior surface 262 and a superior surface 264. The inferior surface 262 of the tibial trial insert 16 is configured to abut the superior surface 32 of the plate 30.

The superior surface 264 includes a pair of curved surfaces 266 positioned opposite the inferior surface 262 and configured to correspond to surfaces of the femoral component 18, as described below. A spine 270 is positioned between the curved surfaces 266 and extends superiorly from the superior surface 264. A pin hole 272 extends medially-laterally between openings 274 formed in the spine 270. The pin hole 272 is configured to receive a pin (described below) to secure the tibial insert trial 16 to the femoral component 18. The pin hole 272 may also be configured to receive bushings that are positioned in each opening 274.

Figure 5:
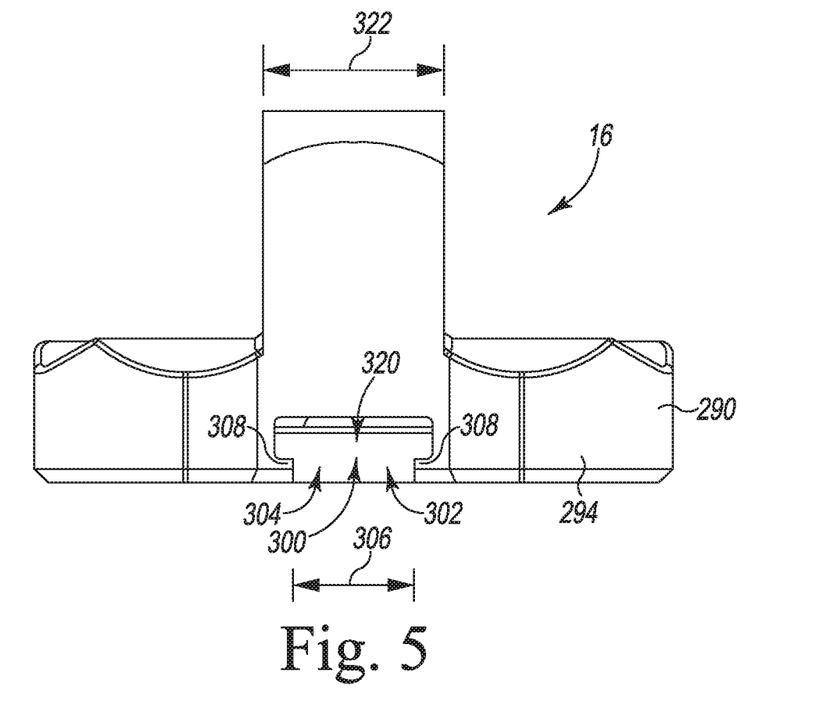
FIG. 5 is a rear elevation view of the tibial insert trial shown in FIG. 1.

The tibial insert trial 16 includes an outer side wall 290 having an anterior section 292 that is shaped to match the anterior section 40 of the tibial base trial 12 and a posterior section 294 that is shaped to match the posterior section 42 of the insert adaptor 14. Referring to FIG. 5, a slot 300 extends through an opening 302 in the posterior section 294 of the outer side wall 290. The slot 300 includes an inferior slot section 304 having a width 306 defined between a pair of flanges 308. The slot 300 also includes a superior slot section 320 that is positioned above and opens into the inferior slot section 304. The superior slot section 320 has a width 322 that is greater than the width 306 of the inferior slot section 304. As described above, the superior slot section 320 is configured to receive the superior flange 70 of the post 58, and the inferior slot section 304 is configured to receive the stem 62 of the post 58.

Figure 6:
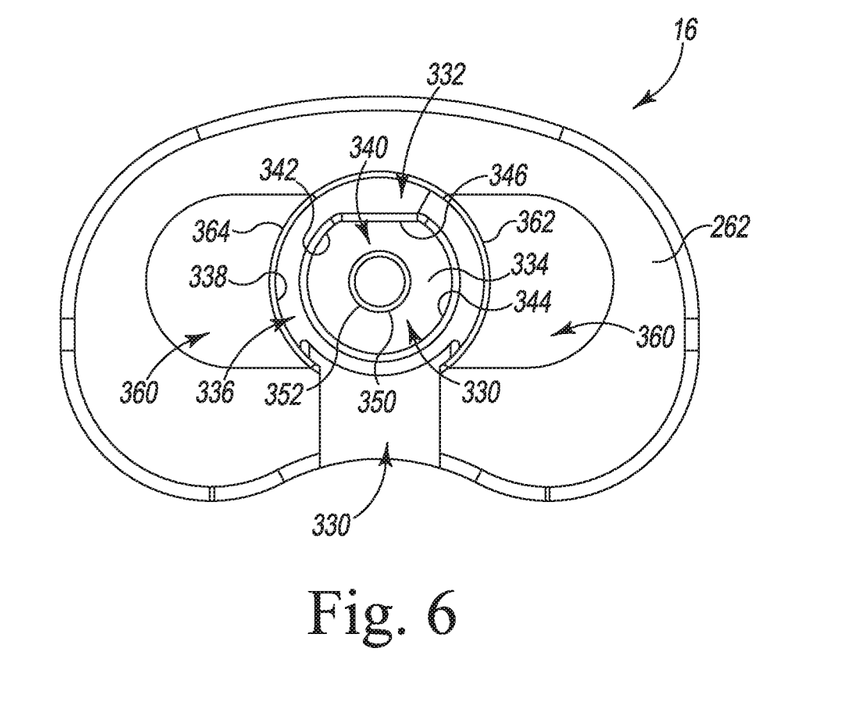
FIG. 6 is a bottom plan view of the tibial insert trial shown in FIG. 1.

Referring to FIG. 6, the slot 300 extends into an aperture 330. The aperture 330 extends from an opening 332 in the inferior surface 262 of the tibial insert trial 16. The aperture 330 extends from the inferior surface 262 to a superior end wall 334. The aperture 330 includes an inferior section 336 defined by an inner side wall 338. The inner side wall 338 is sized and shaped to the outer surface 120 of the base 102 of the insert adaptor 14 so that the inferior section 336 of the aperture 330 receives the base 102 of the insert adaptor 14. A superior section 340 of the aperture is defined by a side wall 342 that extends from the inferior section 336 to the superior end wall 334. The side wall 342 includes a curved surface 344 and a planar anterior surface 346. The curved surface 344 is sized and shaped to correspond to the curved surface 134 of the outer wall 130 of the plug 104. The planar anterior surface 146 is sized and shaped to correspond to the planar anterior surface 136 of the outer wall 130 of the plug 104.

A pin 350 extends inferiorly from the superior end wall 334. The pin 350 includes an outer side wall 352 that is cylindrical. The outer side wall 352 of the pin 350 is sized and shaped to correspond to the inner surface 210 defining the aperture 140. As described in more detail below, when the insert adaptor 14 is coupled to the tibial insert trial 16 the pin 350 is received within the aperture 140 of the insert adaptor 14. The ball 204 of the retention mechanism 200 is configured to engage the outer side wall 352 of the pin 350 to provide friction between the ball 204 and the pin 350.

A pair of finger grooves 360 is formed in the inferior surface 262 of the tibial insert trial 16. One groove 360 is formed on each of a lateral side 362 and a medial side 364 of the aperture 330. The grooves 360 are formed as indents in the inferior surface 262 that are sized to receive a user's fingers. When the insert adaptor 14 is inserted into the tibial insert trial 16, the finger grooves 360 enable a user to grasp the insert adaptor 14 to remove the tibial insert trial 16.

Returning to FIG. 1, the femoral component 18 includes a body 380 having a pair of curved surfaces 382 that are configured to articulate on the curved surfaces 266 of the tibial insert trial 16. A post 384 extends superiorly from the body 380 and is configured to be inserted into a cavity formed in a distal end of a patient's femur. Transverse bores 390 extend in a medial-lateral direction through the body 380. The transverse bores 390 are configured to receive a pin (described below). The pin is configured to pass through each bore 390 and through the pin hole 272 in the spine 270 of the tibial insert trial 16 to secure the femoral component 18 to the tibial insert trial 16.

Figure 7:
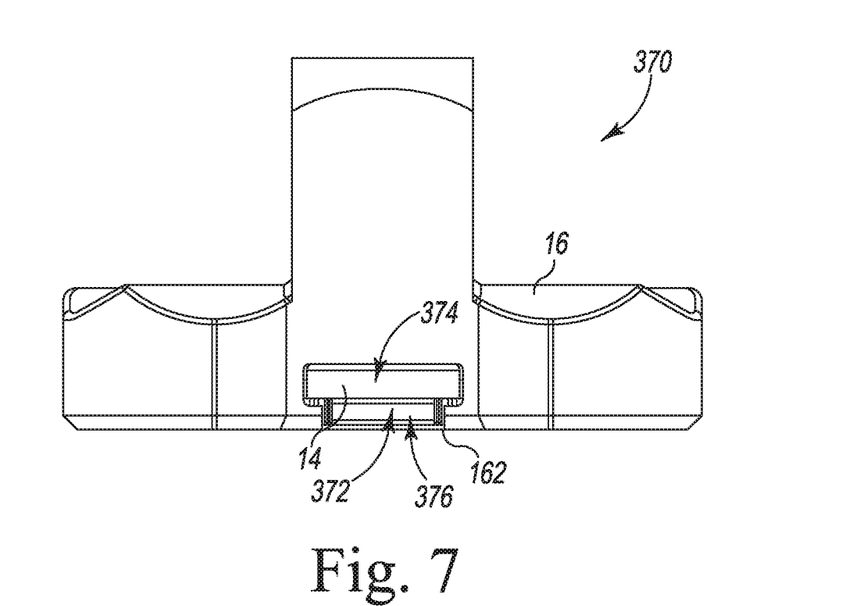
FIG. 7 is a rear elevation view of the insert adaptor inserted into the tibial insert trial shown in FIG. 1.
Figure 8:
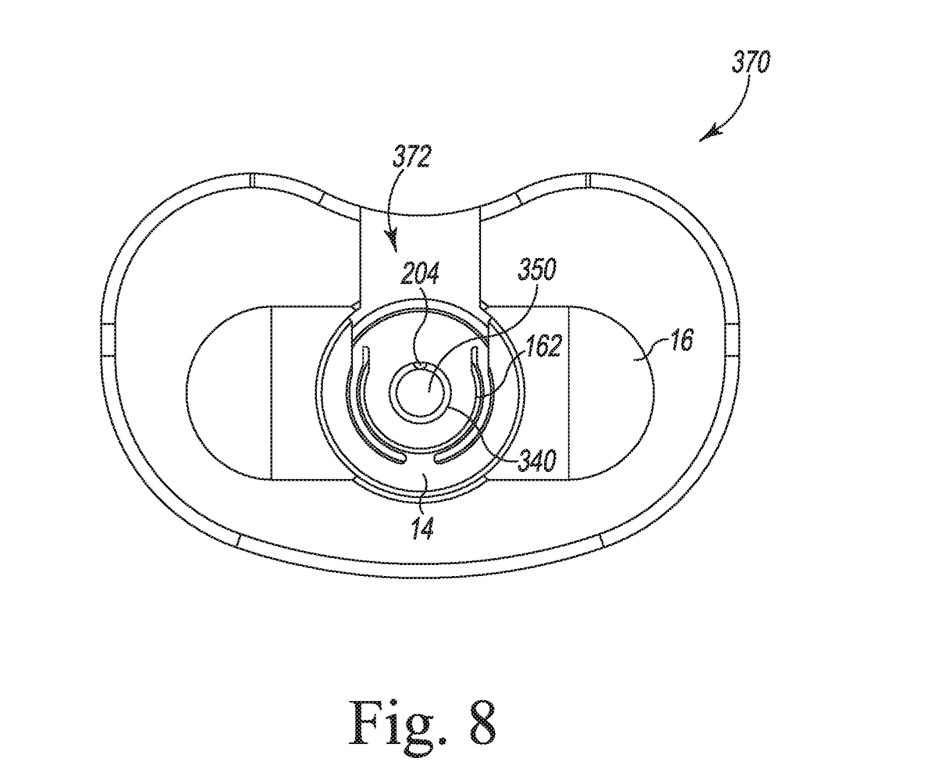
FIG. 8 is a bottom plan view of the insert adaptor inserted into the tibial insert trial shown in FIG. 1.

Referring to FIGS. 7 and 8, the insert adaptor 14 is configured to be inserted into the aperture 330 of the tibial insert trial 16 to secure the insert adaptor 14 within the tibial insert trial 16 to form the tibial trial component 370. Referring to FIG. 7, the plug 104 of the insert adaptor 14 is positioned within the aperture 330 of the tibial insert trial 16. The curved surface 344 of the side wall 342 of the aperture 330 corresponds to and mates with the curved surface 134 of the outer wall 130 of the plug 104. Also, the planar anterior section 346 of the side wall 342 of the aperture 330 corresponds to and mates with the planar anterior surface 136 of the outer wall 130 of the plug 104. The engagement of the planar anterior section 346 and the planar anterior surface 136 facilitates prohibiting the insert adaptor 14 from rotating relative to the tibial insert trial 16.

The pin 350 of the tibial insert trial 16 is positioned within the aperture 140 of the insert adaptor 14. The ball 204 of the retention mechanism 200 extends anteriorly from the inner surface 210 of the aperture 140 to engage the outer side wall 352 of the pin 350. The ball 204 provides friction against the outer side wall 352 of the pin 350 to prevent the insert adaptor 14 from disengaging from the tibial insert trial 16. To remove the insert adaptor 14 from the tibial insert trial 16, as user may position his/her fingers within the finger grooves 360 to grasp the insert adaptor 14 and pull away from the tibial insert trial 16 with a force that overcomes the friction created between the ball 204 and the outer side wall 352 of the pin 350.

The locking tab 162 is positioned such that the opening 192 between the arms 186 faces a posterior passageway 372. Referring to FIG. 8, the posterior passageway 372 defined by the posterior slots 160, 164 of the insert adaptor 14 and the posterior slot 300 of the tibial insert trial 16. The passageway 372 is sized and shaped to receive the post 58 of the tibial base trial 12. The slot 164 of the insert adaptor 14 and the superior slot section 320 of the tibial trial component 370 define a superior passageway section 374 of the passageway 372. The superior passageway section 374 is sized and shaped to receive the superior flange 70 of the post 58. The slot 160 of the insert adaptor 14 and the inferior slot section 304 of the tibial trial component 370 define an inferior passageway section 376 of the passageway 372 that is sized and shaped to receive the stem 62 of the post 58. The inferior passageway section 376 extends between the flanges 308 of the tibial insert trial 16. The locking tab 162 is positioned within the inferior passageway section 376.

The illustrated tibial insert trial 16 is one of a plurality of tibial insert trials that make a multi-piece assembly configured to assist the surgeon in selecting a size and configuration of tibial trial component 370. The insert adaptor 14 may be assembled with one of a number of tibial insert trials 16 to form the tibial trial component 370. In an embodiment, the tibial insert trials 16 may be provided in different sizes and/or configurations. Because the insert adaptor 14 is configured to be secured to each tibial insert trial 16, the surgeon is able to assemble a tibial trial component 370 of one size and configuration, evaluate the performance of that tibial trial component 370, and then modify the tibial trial component 370 as necessary to determine intraoperatively the type and configuration of the tibial trial component 370 to be implanted.

Figure 9:
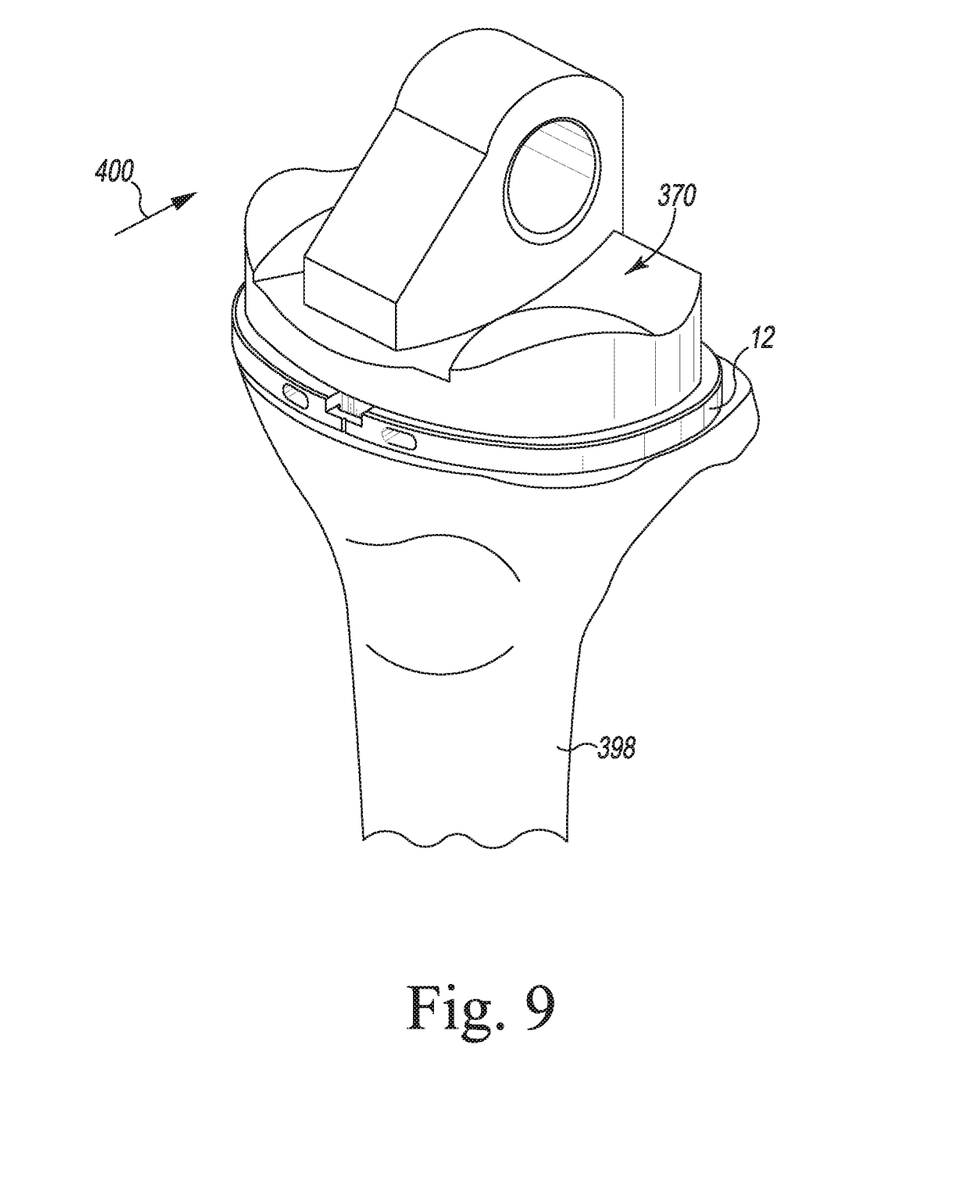
FIG. 9 is a perspective view of a tibial trial component positioned on the proximal end of a patient's tibia.
Figure 10:
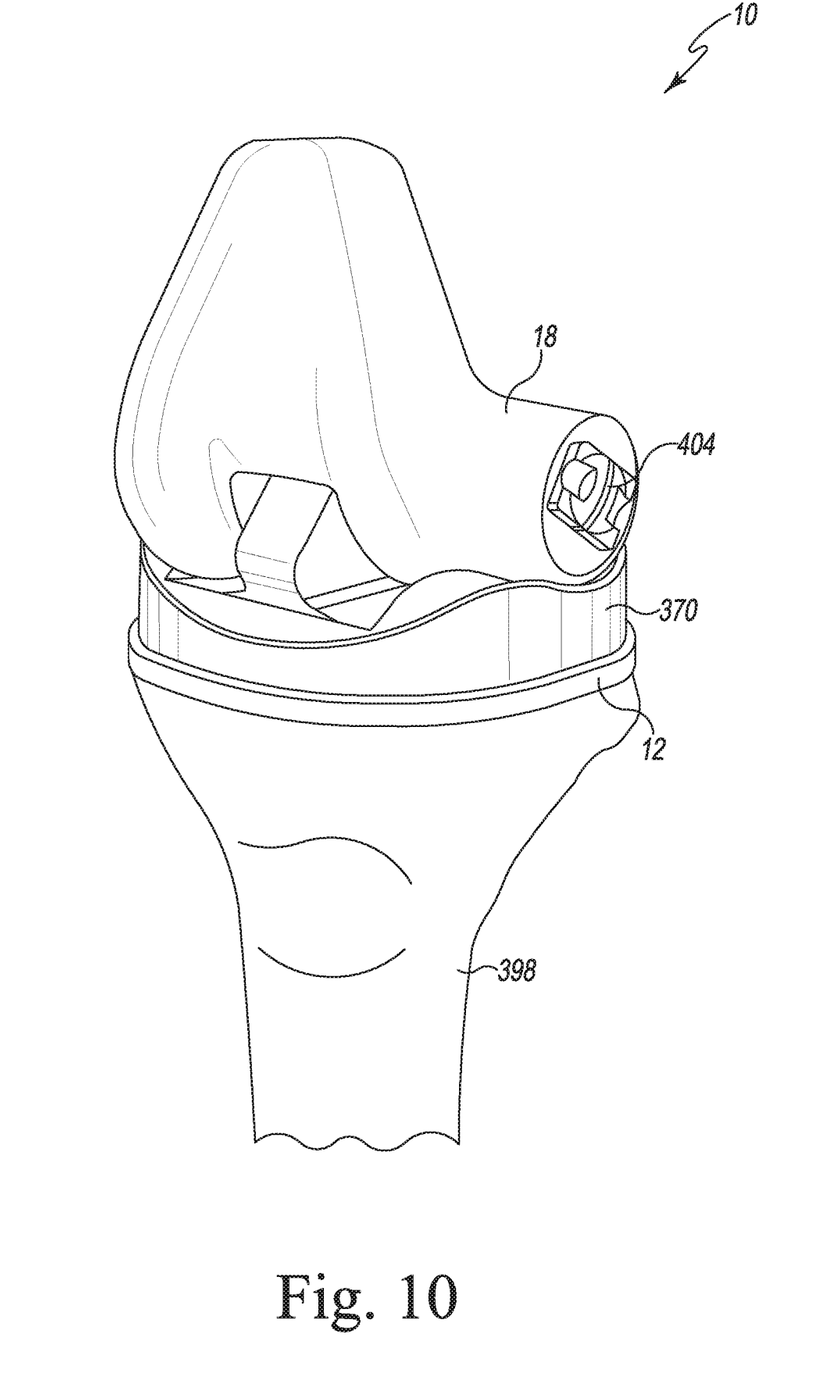
FIG. 10 is a perspective view of the orthopaedic surgical instrument system shown in FIG. 1 assembled on the proximal end of a patient's tibia.
Figure 11:
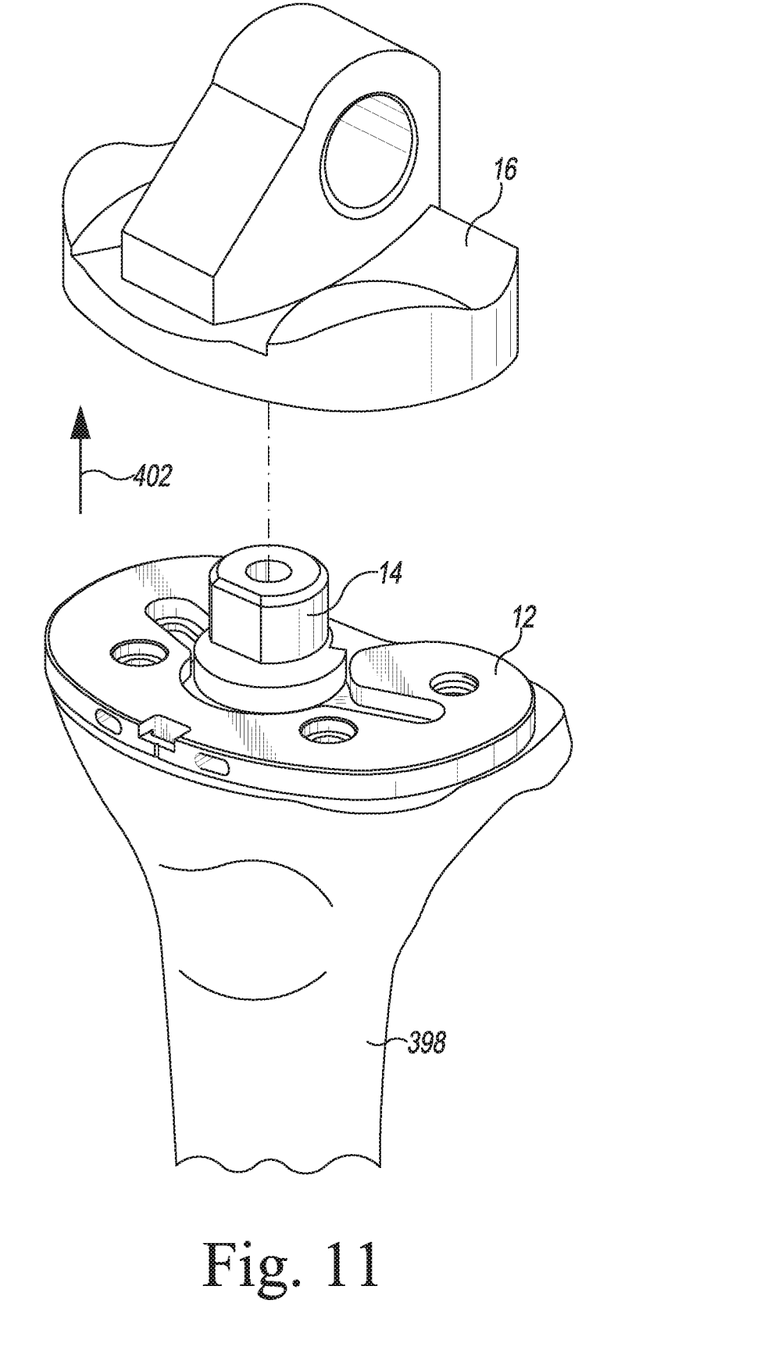
FIG. 11 is a perspective similar to FIG. 9.

Referring now to FIGS. 9-11, portions of an orthopaedic surgical procedure utilizing the system 10 are shown. The surgeon first performs a resection of the proximal end of the patient's tibia 398 to surgically prepare the tibia 398 for trial reduction. For example, the surgically-prepared proximal end of the patient's tibia 398 includes a resected surface configured to receive the tibial base trial 12. In an embodiment where the femoral component 18 is a trial component, the surgeon may also perform a resection of the distal end of the patient's femur to surgically prepare the femur for trial reduction. In an embodiment where the femoral component 18 is a primary femoral component from a previous joint arthroplasty, the surgeon may trial the tibial trial component 370 with the primary femoral component or prepare the distal end of the patient's femur for a secondary femoral component.

The surgeon may perform an initial trial reduction with the instrument system 10. In doing so, the surgeon uses the system 10 to evaluate and check the stability and kinematics of the patient's femur and tibia 398 for implantation of a hinged knee prosthesis. The surgeon also positions the tibial base trial 12 on the resected surface of the patient's tibia 398. The tibial trial component 370 is aligned with the tibial base trial 12 and the surgeon advances the tibial trial component 370 into the gap between the tibial base trial 12 and the femoral component 18. As illustrated in FIG. 9, the tibial trial component 370 is posteriorly advanced in the direction indicated by arrow 400 onto the post 58 of the tibial base trial 12 so that the post 58 is received in the posterior passageway 372 of the tibial trial component 370. The superior flange 70 of the post 58 is received in the superior passageway section 374, and the stem 62 of the post 58 is received in the inferior passageway section 376. As the tibial trial component 370 is posteriorly advanced, the stem 62 of the post 58 passes through the opening 192 between the arms 186 of the locking tab 162. The arms 186 of the locking tab 162 are received within the channel 80 defined between the superior flange 70 of the post 58 and the plate 30 of the tibial base trial 12. The arms 186 of the locking tab 162 deflect outward so that the stem 62 of the post 58 is received in the opening 192 defined between each arm 186. The arms 186 spring back to their original position to engage the stem 62 of the post 58 to secure the locking tab 162 to the post 58, thereby preventing movement of the insert adaptor 14 in an inferior-superior direction relative to the tibial base trial 12. Securing the locking tab 162 to the post 58 secures the tibial trial component 370 to the tibial base trial 12 so that the tibial trial component 370 is permitted to rotate relative to the tibial base trial 12. As can be seen in FIG. 10, the transverse bores 390 of the femoral component 18 are aligned with the pin hole 272 of the tibial trial component 370 and an elongated pin 404 is inserted into the transverse bores 390 and the pin hole 272 to secure the femoral component 18 to the tibial trial component 370. When the femoral component 18 is in place, the surgeon carefully extends the knee of the patient, noting the anteroposterior stability, medial-lateral stability, and overall alignment in the anterior-posterior ("A/P") plane and medial-lateral ("M/L") plane.

As the range of motion is evaluated, the load on the femoral component 18 translates posteriorly as the knee is moved between extension and flexion. The tibial trial component 370 may also be rotated about the axis 60 of the post 58 of the tibial base trial 12. To improve performance, the surgeon may decouple the femoral component 18 from the tibial trial component 370 to exchange the tibial insert trial 16. As illustrated in FIG. 11, the tibial insert trial 16 is detached superiorly by moving the trial 16 in the direction indicated by arrow 402. Because the locking tab 162 is secured to the post 58, superiorly advancing the tibial insert trial 16 overcomes the friction between the ball 204 and the outer side wall 352 of the pin 350 so that the tibial insert trial 16 becomes detached from the insert adaptor 14. The insert adaptor 14 is left secured to the post 58 of the tibial base trial 12 such that another tibial insert trial 16 may be secured to the insert adaptor 14 for trialing. The surgeon may then select a second tibial insert trial 16 to attach to the insert adaptor 14. The surgeon may then trial the second tibial insert trial 16 as discussed above.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of trialing an orthopaedic prosthetic assembly, the method comprising:
  assembling a tibial trial component by aligning an insert adaptor with a tibial insert trial and advancing the insert adaptor into an aperture defined in the tibial insert trial to form the tibial trial component, wherein advancing the insert adaptor into the aperture of the tibial insert trial includes receiving a pin located in the aperture defined in the tibial insert trial into an aperture of the insert adaptor;
  aligning a tibial trial component with a tibial base trial positioned on a proximal end of a tibia of a patient's joint,
  advancing the tibial trial component posteriorly to move a post of the tibial base trial component into a posterior passageway defined in the tibial trial component,
  coupling the tibial trial component to the tibial base trial component such that the tibial trial component is permitted to rotate relative to the tibial base trial,
  aligning a pair of transverse bores defined in a femoral component with a bore defined in a spine of the tibial trial component,
  advancing an elongated pin through the transverse bores and the spine of the tibial trial component to couple the femoral component to the tibial trial component, and
  moving the patient's joint through a range of motion including extension and flexion to evaluate a configuration of the orthopaedic prosthetic assembly corresponding to the tibial base trial and the tibial trial component.

2. The method of claim 1, further comprising:
moving the tibial insert trial of the tibial trial component in a superior direction to detach the tibial insert trial from the insert adaptor of the tibial trial component,
selecting a second tibial insert trial having a different size from the tibial insert trial, and
moving the second tibial insert trial in an inferior direction to attach the second tibial insert trial to the insert adaptor of the tibial trial component.

3. The method of claim 2, wherein moving the tibial insert trial in the superior direction comprises removing the pin of the tibial insert trial from the aperture of the insert adaptor.

4. The method of claim 2, wherein the moving the second tibial insert trial in the inferior direction comprises advancing the insert adaptor into an aperture defined in the second tibial insert trial.

5. The method of claim 4, wherein advancing the insert adaptor into the aperture of the second tibial insert trial includes receiving a pin located in the aperture defined in the second tibial insert trial into the aperture of the insert adaptor.

6. The method of claim 5, wherein receiving the pin located in the aperture defined in the second tibial insert trial into the aperture of the insert adaptor includes engaging an outer side wall of the pin located in the aperture of the second tibial insert trial with a retention mechanism of the insert adaptor to secure the insert adaptor to the second tibial insert trial.

7. The method of claim 6, wherein engaging the outer side wall of the pin located in the aperture of the second tibial insert trial with the retention mechanism of the insert adaptor comprises biasing a ball of the retention mechanism onto the outer side wall of the pin located in the aperture of the second tibial insert trial.

8. The method of claim 2, further comprising advancing the tibial trial component including the second tibial insert trial posteriorly to move the post of the tibial base trial component into a posterior passageway defined in the tibial trial component including the second tibial insert trial.

9. The method of claim 8, wherein advancing the tibial trial component including the second tibial insert trial comprises advancing the tibial trial component including the second tibial insert trial posteriorly to move (i) a superior flange of the post of the tibial base trial component into a superior slot section of the posterior passageway defined in the tibial trial component including the second tibial insert trial and (ii) a stem of the post of the tibial base trial component into an inferior slot section of the posterior passageway defined in the tibial trial component including the second tibial insert trial.

10. The method of claim 8, wherein advancing the tibial trial component including the second tibial insert trial posteriorly comprises engaging a locking tab of the insert adaptor onto the post of the tibial base trial.

11. The method of claim 10, wherein engaging the locking tab of the insert adaptor comprises positioning a pair of arms of the locking tab in a channel of the post.

12. The method of claim 1, wherein receiving the pin located in the aperture defined in the tibial insert trial into the aperture of the insert adaptor includes engaging an outer side wall of the pin located in the aperture of the tibial insert trial with a retention mechanism of the insert adaptor to secure the insert adaptor to the tibial insert trial.

13. The method of claim 12, wherein engaging the outer side wall of the pin located in the aperture of the tibial insert trial with the retention mechanism of the insert adaptor comprises biasing a ball of the retention mechanism onto the outer side wall of the pin located in the aperture of the tibial insert trial.

14. The method of claim 1, wherein advancing the tibial trial component posteriorly comprises advancing the tibial trial component posteriorly to move the post of the tibial base trial component into the posterior passageway defined in the insert adaptor of the tibial trial component.

15. The method of claim 14, wherein advancing the tibial trial component posteriorly comprises advancing the tibial trial component posteriorly to move (i) a superior flange of the post of the tibial base trial component into a superior slot section of the posterior passageway defined in the insert adaptor and (ii) a stem of the post of the tibial base trial component into an inferior slot section of the posterior passageway defined in the insert adaptor.

16. The method of claim 14, wherein advancing the tibial trial component posteriorly comprises engaging a locking tab of the insert adaptor onto the post of the tibial base trial.

17. The method of claim 16, wherein engaging the locking tab of the insert adaptor comprises positioning a pair of arms of the locking tab in a channel of the post.

* * * * *